United States Patent
Khan et al.

(10) Patent No.: US 8,702,785 B2
(45) Date of Patent: Apr. 22, 2014

(54) MIGRATION RESISTANT PROSTHETIC STENT GRAFT FOR TREATMENT OF ABDOMINAL AORTIC ANEURYSM

(75) Inventors: Isaac John Khan, Bridgewater, NJ (US); David C. Majercak, Stewartsville, NJ (US); Jin S. Park, Parsippany, NJ (US); Diana M. Sanchez, Bernardsville, NJ (US)

(73) Assignee: Cordis Corporation

( * ) Notice: Subject to any disclaimer, the term of this patent is extended or adjusted under 35 U.S.C. 154(b) by 518 days.

(21) Appl. No.: 11/323,781

(22) Filed: Dec. 30, 2005

(65) Prior Publication Data
US 2007/0156227 A1    Jul. 5, 2007

(51) Int. Cl.
*A61F 2/06* (2013.01)

(52) U.S. Cl.
USPC ........................................ 623/1.13

(58) Field of Classification Search
USPC ............ 623/1.13, 1.35, 1.16, 1.18, 1.36
See application file for complete search history.

(56) References Cited

U.S. PATENT DOCUMENTS

| | | | |
|---|---|---|---|
| 6,325,819 B1 | 12/2001 | Pavcnik et al. | |
| 6,585,756 B1 * | 7/2003 | Strecker | 623/1.16 |
| 7,267,686 B2 * | 9/2007 | DiMatteo et al. | 623/1.24 |
| 8,012,198 B2 * | 9/2011 | Hill et al. | 623/1.24 |
| 2003/0130724 A1 * | 7/2003 | DePalma et al. | 623/1.16 |
| 2004/0210307 A1 * | 10/2004 | Khairkhahan | 623/2.18 |
| 2005/0090843 A1 | 4/2005 | Bolduc | |
| 2005/0096735 A1 * | 5/2005 | Hojeibane et al. | 623/1.24 |

FOREIGN PATENT DOCUMENTS

| | | |
|---|---|---|
| EP | 1 086 665 A | 3/2001 |
| EP | 1 329 204 A | 7/2003 |
| EP | 1 621 159 A | 2/2006 |
| JP | 2000-516515 A | 2/1998 |
| WO | WO 00/69367 A | 11/2000 |
| WO | WO 03/075798 A | 9/2003 |

OTHER PUBLICATIONS

Japanese Notification of Reasons for Refusal dated May 29, 2012 of corresponding Japanese Patent Application No. 2006-355479.

* cited by examiner

*Primary Examiner* — Tuan V Nguyen
*Assistant Examiner* — Sarah Simpson

(57) ABSTRACT

A prosthetic stent graft for the treatment of AAA includes a plurality of graft legs, each secured in a deployed position by a sealing gasket within a stent segment of the sealing gasket and to one side of a framing bracket. The framing bracket traverses the diameter of the stent segment and extends axially away, dividing the first stent segment into two portions, each portion for receiving a graft leg of the stent graft. The sealing gasket can include a stabilizer having a second generally cylindrical stent segment, and an extension bracket traversing the diameter of the second stent segment and extending away from the second stent segment. The extension bracket and the first bracket are connected with one another at a mutual generally central position.

25 Claims, 4 Drawing Sheets

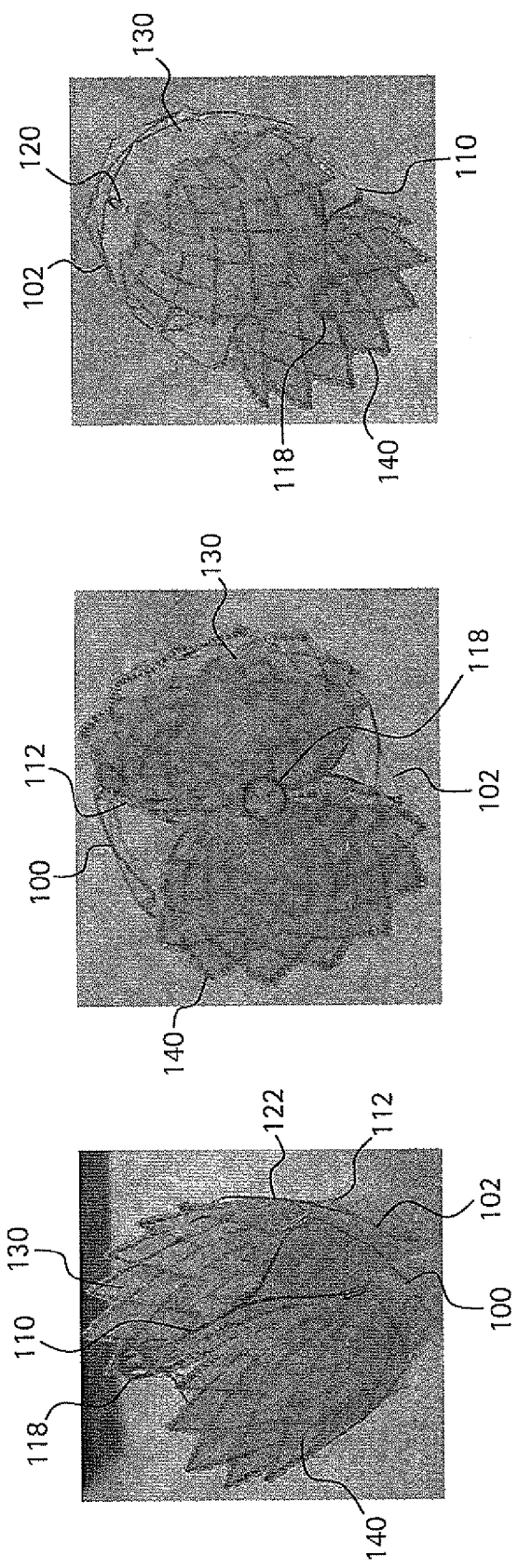

MIGRATION RESISTANT PROSTHETIC STENT GRAFT FOR TREATMENT OF ABDOMINAL AORTIC ANEURYSM

BACKGROUD OF THE INVENTION

1. Field of Invention

The invention relates to the field of medical devices, and more specifically to a prosthesis for the treatment of vascular disease, particularly abdominal aortic aneurysm.

2. Description of Related Art

Vascular disease is a leading cause of premature mortality in developed nations, often presenting as a vascular aneurysm. A vascular aneurysm is a localized dilation of a vessel wall, due to thinning or weakness of the wall structure, or separation between layers of the vessel wall. If untreated, the aneurysm may burst and hemorrhage uncontrollably. Aneurysms are particularly dangerous and prevalent in the aorta, because the aorta supplies blood to all other areas of the body, and because the aorta is subject to particularly high pressures and stresses accordingly. Rupture of an aortic aneurysm is the $15^{th}$ leading cause of death in the United States, afflicting 5% of older men.

Aortic aneurysms are described by their position. They are either thoracic, generally between the aortic arch and the junction of the left and right renal arteries, or abdominal, between the junction of the renal arteries and the branch of the iliac arteries.

It is known to treat vascular aneurysms surgically where blood pressure control medication is unsuccessful at arresting growth of the aneurysm. Surgery often involves the insertion of a vascular stent graft to exclude the aneurysm and carry blood past the dilated portion of the vessel, relieving the pressure on the aneurysm. Designing a viable stent graft for the treatment of abdominal aortic aneurysm (AAA) is particularly challenging, in part because the graft must branch to follow the shape of the abdominal aorta to carry blood into the separate iliac arteries without obstruction.

Moreover, it would be advantageous to design a stent graft that is collapsible to facilitate percutaneous insertion by minimally invasive surgical techniques. Additionally, the stent graft must remain in the proper position after deployment and for years of continuous use. Accordingly it would be advantageous to design a stent graft that can be secured in position by minimally invasive surgical techniques. Further, it would be advantageous for a stent graft to have superior positional stability once deployed.

Further, known AAA stents with supra-renal stabilization include a stent segment that traverses the junction of the renal arteries. This creates a phenomenon called 'jailing' or 'caging' of the renal arteries, where the circumference of the stent structure partially obstructed and therefore interferes with blood flow to the renal arteries. Moreover, such stents as described lack flexibility, both in delivery configuration and in deployed configuration, due to the long length of the circumferential stent structure. Therefore, an improved AAA stent graft that has supra-renal stabilization while maintaining adequate transverse flexibility and avoiding interference with renal blood flow would be desirable.

BRIEF SUMMARY OF THE INVENTION

Therefore, provided according to the present invention is a prosthetic vascular stent graft, and particularly a sealing gasket therefor, the sealing gasket comprising a generally cylindrical first stent segment. A framing bracket traverses the diameter of the first stent segment and extends away from the first stent segment. The first framing bracket divides the first stent segment into two portions, each portion for receiving a graft leg of the stent graft.

A vascular graft portion can be supported by, more preferably surrounds and/or is secured to, the first stent segment. Structure of the sealing gasket preferably comprises a shape memory material, more preferably Nitinol and/or an alloy comprising Nitinol. A centrally located tip at of the framing bracket can extend laterally to either side of the framing bracket, and hold, secure or guide an inner core of the stent delivery device.

A plurality of inwardly and/or outwardly directed barbs on the circumference of the sealing gasket secure the sealing gasket to the vessel, and or to the graft legs to resist migration of either. Compressible sealing foam and/or a segment of vascular graft material can be secured to an inner surface of the first stent segment adjacent to each junction of the framing bracket with the first stent segment.

In a further embodiment, the sealing gasket has a stabilizer portion. The stabilizer portion includes a second generally cylindrical stent segment, and an extension bracket traversing the diameter of the second stent segment and extending away from the second stent segment. The extension bracket and the first bracket are connected with one another at a mutual generally central position.

In any of the foregoing embodiments, the stent graft includes a plurality of graft legs, each positioned in a respective portion of the first stent segment of the sealing gasket and to one side of the first framing bracket.

BRIEF DESCRIPTION OF THE DRAWINGS

These and other features, benefits, and advantages of the present invention will be made apparent with reference to the following detailed description, appended claims, and accompanying figures, wherein like reference numerals refer to like structures across the several views, and wherein:

FIG. 5 illustrates a first perspective view of a prototype first exemplary embodiment of the stent graft according to the present invention;

FIG. 6 illustrates a top plan view of the prototype first exemplary embodiment of the stent graft according to the present invention;

FIG. 7 illustrates an alternate perspective view of the prototype first exemplary embodiment of the stent graft according to the present invention;

DETAILED DESCRIPTION OF THE INVENTION

Figure 1:
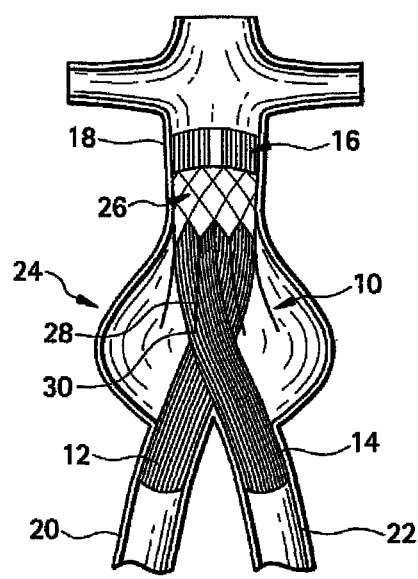
FIG. 1 illustrates a prosthetic AAA stent graft according to the prior art.

Referring now to FIG. 1, illustrated is a prior art prosthetic stent graft, generally 10, for the treatment of AAA. The prior art stent graft 10 includes two graft legs, 12, 14, which carry arterial blood from a cephalid region 16 of the abdominal aorta 18, and into the iliac arteries 20, 22, respectively, thereby excluding the aneurysm 24. Graft legs 12, 14 are generally circular deployed cross-section, except for where they are held in position in the abdominal aorta 18 by sealing gasket 26. The graft legs 12, 14 are held substantially flat against one another within sealing gasket 26. Recapture legs 28 depend from sealing gasket 26 and have widened structure 30 at their distal ends to secure the sealing gasket 26 against structure of the delivery apparatus provided for that purpose when crimped for delivery.

Figure 2:
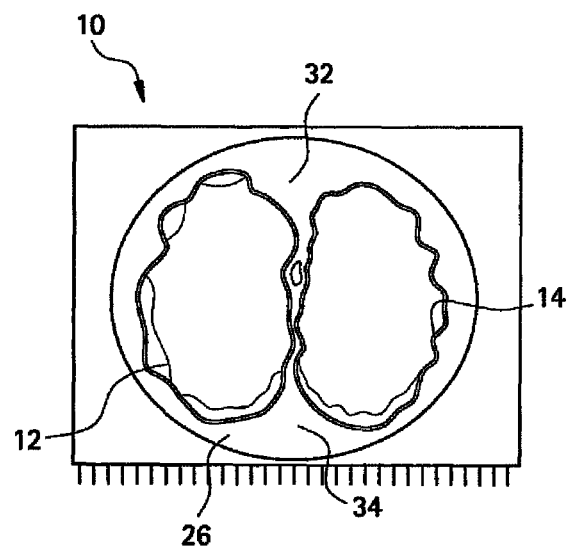
FIG. 2 illustrates a top axial plan view of the prior art stent graft of FIG. 1.

Referring now to FIG. 2, shown is an axial view of the inlet to stent graft 10. Spaces 32, 34 between the sealing gasket 26 and graft legs 12, 14 are filled with a thickened foam to prevent blood flow past the sealing gasket 26 except through graft legs 12, 14.

The prior art described above suffered primarily from a problem of migration by the graft legs 12, 14. This was in part because the graft legs 12, 14 are held in position within the sealing gasket 26 by the tendency of the graft legs 12, 14 to expand to a diameter beyond that permitted by sealing gasket 26. As a result, it is necessary to deploy graft legs 12, 14 simultaneously when using sealing gasket 26.

Figure 3:
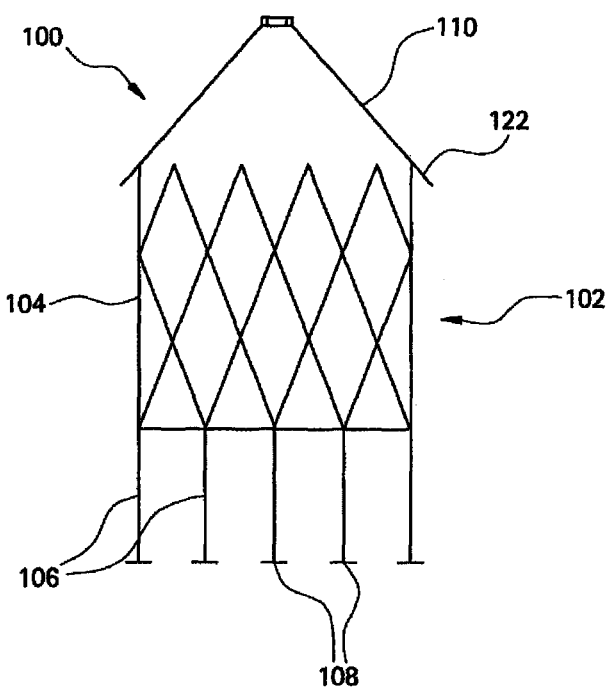
FIG. 3 illustrates a schematic axial cross-section of a prosthetic stent sealing graft according to a first exemplary embodiment of the present invention.

Therefore, referring now to FIG. 3, provided according to the present invention is a sealing gasket, generally 100, for a stent graft treating AAA. Sealing gasket 100 has a generally cylindrical stent segment 102 which supports, and is preferably surrounded by and secured to a generally cylindrical graft material 104. Recapture legs 106 depend from the sealing gasket 100 and have widened structure at their distal ends 108 to secure the sealing gasket 100 against structure of the delivery apparatus provided for that purpose when crimped for delivery. However, as compared to the prior art sealing gasket 26, recapture legs 106 are shorter, and are preferably no longer than about as long as the diameter of stent segment 102. The shortened recapture legs 106 reduces the range of movement of ends 108, and reduces the likelihood and severity of wear caused by ends 108 on the fabric of the graft legs.

Figure 4:
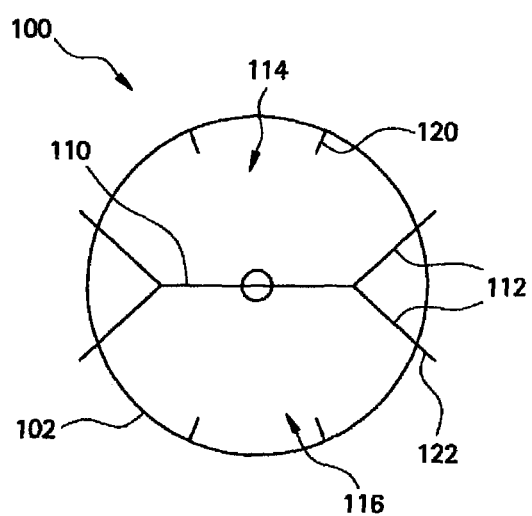
FIG. 4 illustrates a schematic top plan view of a prosthetic stent sealing graft according to a first exemplary embodiment of the present invention.

An upstream or cephalid end of the sealing gasket 100 includes a framing bracket 110 extending in a cephalid direction and generally traversing the diameter of stent segment 102. Referring now to FIG. 4, the sealing gasket 100 is illustrated in an axial plan view. Framing bracket 110 includes two support legs 112 on each side thereof. Support legs 112 connect to the framing bracket 110 at an angle with one another, and connect with the stent segment 102 at different positions around the circumference of the stent segment 102. Together with stent segment 102, framing bracket 110, including support legs 112, defines two windows 114, 116, through which graft legs may pass to be secured by the sealing gasket 100. Accordingly, a graft leg would have full circumferential support by the structure defining windows 114, 116, and graft legs could be deployed individually. Additionally, framing bracket 110 includes a centrally located connecting member, for example, a C-shaped tip 118, at mid-portion. The C-shaped tip 118 assists to hold and support a cylindrical inner core of the percutaneous delivery device in its delivery configuration prior to their deployment. The open portion of the C-shaped tip 118 permits release of the inner core of the delivery device upon deployment of the sealing gasket 100. The lateral extension of the C-shaped tip 118 into windows 114, 116 obstructs any movement of the deployed graft legs in the cephalid or cranial direction.

Other shapes besides C-shape are applicable to the centrally located connecting member. For example, U-shape, V-shape or a diamond shape having one corner open are applicable as well. The preferred tip merely accommodates a central core of the delivery catheter, is open to one side at the framing bucket 110, and/or extends laterally into windows 114, 116.

Sealing gasket 100 preferably includes one or more inwardly directed barbs 120 at or near the cephalid portion of the stent segment 102 and on the circumference of windows 114, 116, to engage the graft legs by their fabric or structure to help secure their position once deployed. Moreover, one or more outwardly directed barbs 122, preferably contiguous with and/or an extension of support leg 112. Where barbs 122 are contiguous with support leg 112 or more generally framing bracket 110, they are self-flaring, since they will flare outward with the expansion of the sealing gasket 100. Barbs 122 engage the vessel wall to resist migration of the sealing gasket 100, and resist migration of the graft legs held by sealing gasket 100 as well, once the graft legs are deployed and engaged with sealing gasket 100.

FIGS. 5-7 offer a view of a prototype sealing gasket 100 according to the first embodiment of the present invention, and deployed graft legs 130, 140. A compressible foam material, omitted from these figures for clarity of illustration, can be placed in the space between sealing gasket 100 and graft legs 130, 140, to prevent blood flow beyond the sealing gasket 100 except through graft legs 130, 140. The compressible foam sections are generally aligned with the point of connection between the framing bracket 110 and the stent segment 102. Alternately or additionally, a section of vascular graft material can be secured between support legs 112 and the circumference of cylindrical stent segment 102 to inhibit blood flow beyond sealing gasket 100 outside graft legs 130, 140.

Figure 8:
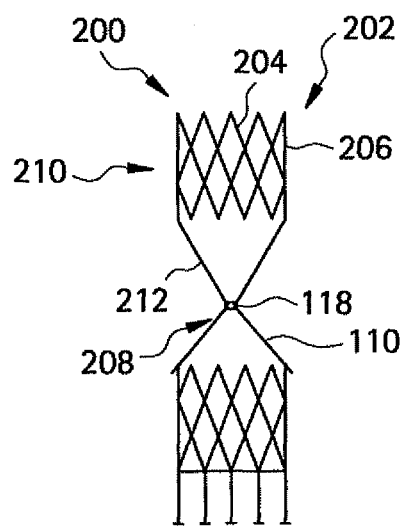
FIG. 8 illustrates a schematic axial cross-section of a prosthetic stent sealing graft according to a second exemplary embodiment of the present invention.
Figure 9:
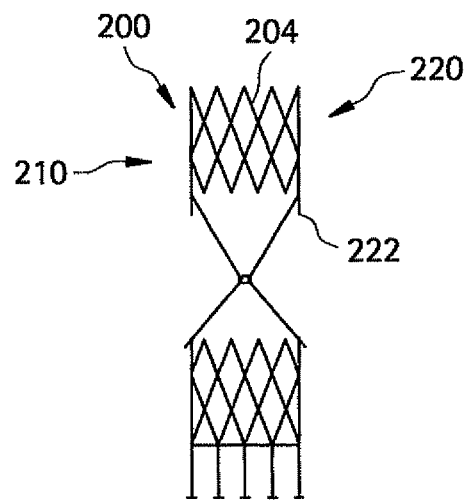
FIG. 9 illustrates a schematic axial cross-section of a prosthetic stent sealing graft according to a third exemplary embodiment of the present invention.
Figure 10:
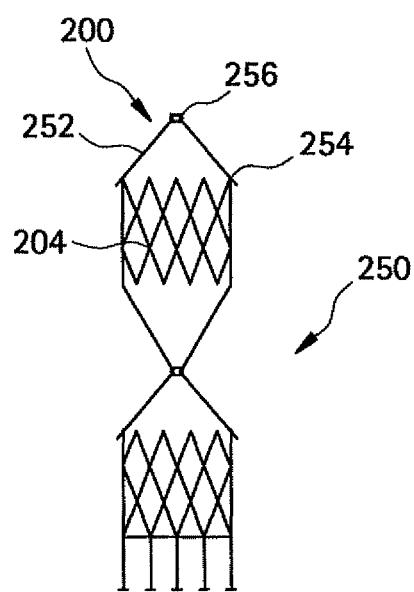
FIG. 10 illustrates a schematic axial cross-section of a prosthetic stent sealing graft according to a fourth exemplary embodiment of the present invention.

Referring now to FIGS. 8-10, illustrated are three additional embodiments of the present invention, each characterized by a supra-renal stabilizer portion, generally 210, which extends in a cephalid direction of the sealing gasket, generally 200. The stabilizer 210 helps to resist migration in the sealing gasket 200, among other benefits. In application, stabilizer 210 will be located in the thoracic aorta, i.e., above the junction of the renal arteries.

Referring now to FIG. 8, a particular embodiment of the sealing gasket, 202, is illustrated. A detailed description of features similar to those already described with respect to the first embodiment will be omitted. Stabilizer 210 includes a generally cylindrical stent segment 204. Stent segment 204 is connected to the sealing gasket 202 at a central point 208 defined by the junction of framing bracket 110 and an extension bracket 212. Central point 208 may be C-shaped tip 118. Extension bracket 212 generally traverses the diameter of stent segment 204.

Referring now to FIG. 9, another embodiment of the sealing gasket, 220, is illustrated. In addition to the features described with respect to sealing gasket 202 of FIG. 8, sealing gasket 220 includes longitudinally extending barbs 222 at a downstream end of stabilizer 210. Barbs 222 engage the wall of the vessel to resist caudal migration.

Referring now to FIG. 10, yet another embodiment of the sealing gasket, 250, is illustrated. Sealing gasket 250 includes a framing bracket 252 generally traversing the diameter of stent segment 204. Framing bracket may include support legs in the same manger as framing bracket 110, and may further include outwardly directed barbs 254, optionally integral with framing bracket 252 or support legs thereof, in the same manner as framing bracket 110. Framing bracket 252 may be joined at a central connecting member, e.g. C-shaped tip 256, in the same manner as C-shaped tip 118 of framing bracket 110, providing similar benefits of C-shaped tip 118 as to securing an inner core of the stent delivery apparatus.

The stabilizer 210 according to the present invention has certain advantages over prior devices. In the first case, the manner of joining stabilizer 210 with sealing gasket 200 minimizes interference with renal blood flow. Further, the manner of joining stabilizer 210 with sealing gasket 200 improves transverse flexibility of the sealing gasket 200 as compared with prior devices.

Stent segments 102, 210, or any associated structure thereof preferably comprises a shape memory material, a group that includes, but is not limited to, Nitinol or a Nitinol alloy. Examples of the latter include Nitinol Niobium (NiTi—Nb), Nitinol Platinum (NiTi—Pt), or Nitinol Tantalum (NiTi—Ta). Stent segments 102, 210, etc., can be formed by cutting the stent from a cylindrical tube of Nitinol or a Nitinol alloy, for example by a laser-cutting technique as is known in the art.

The present invention has been described herein with reference to certain exemplary or preferred embodiments. These embodiments are offered as merely illustrative, not limiting, of the scope of the present invention. For example, the exemplary embodiment is described in the context of treating AAA. However, the invention is not limited to that purpose, and is applicable as a sealing gasket for any prosthetic implant. The sealing gasket is also applicable to seal more or fewer than two grafts in other applications. Certain other alterations or modifications may be apparent to those skilled in the art in light of instant disclosure without departing from the spirit or scope of the present invention, which is defined solely with reference to the following appended claims.

The invention claimed is:

1. A sealing gasket for a prosthetic vascular stent comprising:
   a generally cylindrical first stent segment, having a longitudinal axis, a cephalid end and a caudal end; and
   a framing bracket comprising a single elongate member and only two pair of support legs on each side of the single elongate member, the framing bracket traversing a diameter of the first stent segment and configured to divide the cephalid end of the first stent segment into two substantially equal sized windows when viewed in cross-section from the cephalid end in plan view, each window configured for receiving a graft leg, the framing bracket being positioned longitudinally offset from the first stent segment and substantially perpendicular to, and symmetric about, the longitudinal axis via the two pair of support legs, wherein the two pair of support legs angle in towards one another, forming an inverted V with an apex and two free ends, and towards the center of the first stent segment, the two pair of support legs are 180 degrees apart from one another and are connected to the single elongate member at their respective apexes in a roof like structure with the free ends of the two pair of support legs extending past the perimeter of the first stent segment thereby forming barbs, the framing bracket also comprising a centrally located connecting member mounted thereto and configured for mating with a delivery device.

2. The sealing gasket according to claim 1, further comprising a first vascular graft portion supported by the first stent segment.

3. The sealing gasket according to claim 2, wherein the first graft portion surrounds the first stent segment.

4. The sealing gasket according to claim 2, wherein the first graft portion is secured to the first stent segment.

5. The sealing gasket according to claim 1, wherein the sealing gasket further comprises a shape memory material.

6. The sealing gasket according to claim 5, wherein the shape memory material comprises one or more of Nitinol and an alloy comprising Nitinol.

7. The sealing gasket according to claim 1, wherein the first framing bracket comprises a centrally located connecting member.

8. The sealing gasket according to claim 7, wherein the connecting member extends laterally to either side of the first framing bracket.

9. The sealing gasket according to claim 1, wherein the first framing bracket is connected with the first stent segment at each side of the first framing bracket by a plurality of support members, the support members forming an angle with one another and connected with the first stent segment at different positions around the circumference thereof.

10. The sealing gasket according to claim 9, further comprising a first plurality of outwardly directed barbs positioned on the circumference of the first stent segment and contiguous with the support members of the first framing bracket.

11. The sealing gasket according to claim 1, further comprising a plurality of recapture legs connected to the first stent segment and extending axially away from the first stent segment in an opposite direction from the first framing bracket.

12. The sealing gasket according to claim 11, wherein the recapture legs are no longer than about a deployed diameter of the generally cylindrical first stent segment.

13. The sealing gasket according to claim 1, further comprising a second plurality of inwardly directed barbs positioned on the circumference of the first stent segment.

14. The sealing gasket according to claim 1, further comprising a third plurality of outwardly directed barbs positioned on the circumference of the first stent segment.

15. The sealing gasket according to claim 14, wherein the third plurality of outwardly directed barbs are contiguous with the first framing bracket.

16. The sealing gasket according to claim 1, further comprising two generally opposed sections of compressible sealing foam secured to an inner surface of the first stent segment adjacent to each junction of the first framing bracket with the first stent segment.

17. The sealing gasket according to claim 1, further comprising a portion of vascular graft material obstructing the space between the sealing gasket and a graft leg.

18. The sealing gasket according to claim 1, further comprising a stabilizer portion, the stabilizer portion having a second generally cylindrical stent segment, an extension bracket generally traversing the diameter of the second stent segment and extending in an axial direction away from the second stent segment, wherein the extension bracket and the first framing bracket are connected with one another at a generally central position of the extension bracket and the first framing bracket.

19. The sealing gasket according to claim 18, wherein the first framing bracket and extension bracket are joined at a mutually shared central connecting member at the center of both the first framing bracket and the extension bracket.

20. The sealing gasket according to claim 18, further comprising a plurality of longitudinally extending barbs projecting from the second stent portion and in a direction of the extension bracket.

21. The sealing gasket according to claim 18, further comprising a second framing bracket traversing a diameter of the second stent segment and extending in an axial direction away from the second stent segment and away from the extension bracket.

22. The sealing gasket according to claim 18, further comprising a fourth plurality of outwardly extending barbs on the circumference of the second stent segment.

23. The sealing gasket according to claim 22, wherein the fourth plurality of outwardly directed barbs are contiguous with the second framing bracket.

24. The sealing gasket according to claim 18, wherein the second framing bracket comprises a centrally located connecting member.

25. The sealing gasket according to claim 18, wherein the first framing bracket and the extension bracket separate the first stent segment and the second stent segment by at least a distance sufficient to prevent the first stent segment or the second stent segment from interfering with blood flow to the renal arteries of a human patient when deployed across the renal arterial junction of the aorta.

* * * * *